(12) United States Patent
Hagel (10) Patent No.: US 9,480,817 B2
(45) Date of Patent: Nov. 1, 2016

(54) URINARY CATHETER ASSEMBLY

(71) Applicant: Coloplast A/S, Humlebaek (DK)

(72) Inventor: Bent Hagel, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 127 days.

(21) Appl. No.: 14/360,626

(22) PCT Filed: Nov. 26, 2012

(86) PCT No.: PCT/DK2012/050433
§ 371 (c)(1),
(2) Date: May 26, 2014

(87) PCT Pub. No.: WO2013/075725
PCT Pub. Date: May 30, 2013

(65) Prior Publication Data
US 2014/0262860 A1    Sep. 18, 2014

(30) Foreign Application Priority Data

Nov. 25, 2011  (DK) .................. 2011 70651
Nov. 25, 2011  (DK) .................. 2011 70652
Nov. 25, 2011  (DK) .................. 2011 70653

(51) Int. Cl.
*A61M 25/00*    (2006.01)
*A61F 5/44*    (2006.01)
*A61M 25/01*    (2006.01)

(52) U.S. Cl.
CPC .............. *A61M 25/002* (2013.01); *A61F 5/44* (2013.01); *A61M 25/0111* (2013.01); *A61M 2025/0046* (2013.01); *A61M 2025/0175* (2013.01); *A61M 2202/0496* (2013.01)

(58) Field of Classification Search
CPC .......... A61M 25/002; A61M 25/0111; A61M 25/0017; A61M 2025/0062; A61M 25/00; A61M 2202/0496; A61M 2025/0046; A61M 2025/0175; A61F 5/44
USPC .................. 206/363–365, 210, 370; 604/265
See application file for complete search history.

(56) References Cited

U.S. PATENT DOCUMENTS

| | | | |
|---|---|---|---|
| 3,794,042 A * | 2/1974 | De Klotz | ................. A61F 5/44 206/210 |
| 5,217,114 A | 6/1993 | Gadberry et al. | |
| 6,634,498 B2 * | 10/2003 | Kayerød | ............... A61L 29/085 206/210 |
| 7,766,163 B2 * | 8/2010 | Tanghoej | ............ A61M 25/002 206/210 |

(Continued)

FOREIGN PATENT DOCUMENTS

| | | |
|---|---|---|
| CN | 101489619 A | 7/2009 |
| CN | 101803968 A | 8/2010 |
| CN | 103747831 A | 4/2014 |
| EP | 1852139 | 11/2007 |
| WO | 9811932 | 3/1998 |
| WO | 03002179 A2 | 1/2003 |
| WO | 2007146820 | 12/2007 |
| WO | 2008009590 | 1/2008 |

*Primary Examiner* — Chun Cheung
(74) *Attorney, Agent, or Firm* — Coloplast Corp., Coloplast A/S; Nick Baumann (57) ABSTRACT

The present invention provides a urinary catheter assembly which comprises at least one urinary catheter for collecting urine from a body opening and a collecting bag connected to the catheter, in a way that a urinary flow can be established in a flow path from the catheter into the bag. The assembly further comprises a catheter package with a container and a cover. The container forms an accommodation for an insertable part of the catheter, and the cover forms a cavity for the collecting bag. The cover is releasably fixed to the container. Furthermore, the package forms an overlap in which the cavity partly covers the accommodation.

16 Claims, 5 Drawing Sheets

(56) References Cited

U.S. PATENT DOCUMENTS

| | | | |
|---|---|---|---|
| 8,181,778 B1 * | 5/2012 | van Groningen | A61M 25/002 206/210 |
| 8,425,491 B2 * | 4/2013 | Tanghoj | A61M 25/0017 600/29 |
| 8,579,115 B2 * | 11/2013 | Murphy | A61L 2/26 206/363 |
| 2003/0004496 A1 | 1/2003 | Tanghoej | |
| 2003/0060807 A1 | 3/2003 | Tanghoej et al. | |
| 2004/0158231 A1 | 8/2004 | Tanghoej et al. | |

* cited by examiner

URINARY CATHETER ASSEMBLY

TECHNICAL FIELD

The present invention relates to a urinary catheter assembly comprising a urinary catheter and a collecting bag.

BACKGROUND OF THE INVENTION

Urinary catheter assemblies for draining the bladder are increasingly used for intermittent as well as indwelling or permanent catheterisation. An intermittent urinary catheter is in most cases a single-use product used to immediately drain the bladder by inserting the catheter into the urethra. After drainage of the bladder, the catheter is withdrawn from the urethra again. This procedure normally takes less than ½ hour, typically 10 minutes. An important feature for the intermittent catheter is to ease the insertion into the urethra. This is done by providing the intermittent catheter with a low frictious surface. Non-limiting examples of such are hydrophilic coated catheters which are subsequently wetted by a swelling medium in order to produce a low friction surface, or oil or water based gel which is applied to the catheter before insertion into the urethra.

Indwelling catheters, as the name also implies, dwells in the body for at least some time. Contrary to intermittent catheters, an indwelling catheter is inserted by a trained professional, typically a physician or a nurse and is left inside the patient for days or weeks. As the indwelling catheter is left inside the patient for a considerable amount of time, such catheters will typically be larger in size and have a different surface compared to intermittent catheters. As an example, hydrophilic coated catheters, where the coating absorbs a considerable amount of liquid for a low frictious surface (swelling degree >100%), will not be suitable for indwelling catheters, because the hydrophilic surface coating would stick inside the mucosa of the urethra if left inside the body for a longer period, due to the hydrophilic coating transforming from being highly lubricious when fully wetted to being adhesive when the hydration level of the coating is reduced.

Typically, urinary catheters are used by patients suffering from urinary incontinence or by disabled individuals like paraplegics or tetraplegics, who may have no control permitting voluntary urination and for whom catheterisation may be the way of urinating.

Normally, the urine is submitted from the urinary catheter directly into the toilet. However, urinary catheters exist in combination with bags for collecting the urine. Typically, such combined devices are of a considerable length and may therefore be troublesome to handle and to bring along, not least for the individuals for whom catheterisation is a daily-life procedure, wherein catheterisation takes place several times a day and wherein the used urinary draining devices must be disposed via the garbage collection.

SUMMARY OF THE INVENTION

It is an object of embodiments of the present invention to provide an improved urinary catheter assembly, and particularly, to provide a more compact assembly.

In a first aspect, the invention provides a urinary catheter assembly comprising at least one urinary catheter for collecting urine from a body opening and a collecting bag connected to the catheter, in a way that a urinary flow can be established in a flow path from the catheter into the bag, the assembly further comprises a catheter package with a container and a cover, the container forms an accommodation for an insertable part of the catheter, the cover forms a cavity for the collecting bag and the cover is releasably fixed to the container, wherein the package forms an overlap in which the cavity partly covers the accommodation.

The urinary catheter may be a standard urinary draining device having well-known dimensions and characteristics.

The collecting bag may be formed integrally with the urinary catheter. This may especially be an advantage for disabled users, such as paraplegics or tetraplegics, who may experience severe difficulties in accessing toilets, thus making the use of the urinary catheter assembly independent of the accessibility of toilets.

The collecting bag may comprise a compartment between sheets of a foil material. The walls of the collecting bag may be coated to facilitate separation of the sheets. It is especially preferred if the coating is in the form of a hydrophilic polymer, such as a coating conventionally being used for coating of e.g. catheters for intermittent catheterisation. The properties of such coatings are very similar to and considered safe for use in contact with mucosal surfaces and may suitably be those disclosed in U.S. Pat. No. 5,001,009 or European Application No. 991701, which will readily adhere to a collecting bag wall made from the materials conventionally used in the art. The collecting bag may as an example be made of flexible materials, such as a polymer film i.e. Poly Vinyl Chloride (PVC), Poly Ethylene (PE) or Poly Ethylene copolymers (such as but not limited to EVA, EMA, EEA, EBA), Poly Propylene (PP), Poly Amide (PA), Thermoplastic Elastomers or any sandwich configuration, including tie layers, comprising any of the mentioned materials.

To ensure a clean and antiseptic assembly, the assembly comprises a catheter package with a container and a cover. The container forms an accommodation for an insertable part of the catheter, whereas the cover, which may be seen as a lid forms a cavity for the collecting bag. Thus, the collecting bag may be shielded and hidden in the cover, so that the collecting bag is protected and cannot be seen before removing the cover from the container. As the cover and the container may be transparent or translucent, the collecting bag may, however, be at least partly seen through the cover. It should be understood that the catheter and the collecting bag may be integral units in the catheter package.

In order to provide a compact assembly, the package forms an overlap in which the cavity covers partly the accommodation. This may e.g. be achieved by folding and/or coiling at least a part of the collecting bag around the catheter when arranging the catheter and the collecting bag in the package. Due to the overlap, the length of the package is reduced.

In one embodiment, the overlap constitutes at least 10% of the total length of the catheter package.

In a cross section perpendicular to the longitudinal direction, the package may be circular or may have an oval, e.g. an elliptical shape. It should be understood, that the longitudinal direction of the package is the direction substantially parallel to the longest dimension of the package. The catheter may be positioned substantially coaxially in the container. The container and cover may preferably be made of materials such as Poly Propylene (PP), Poly Ethylene (PE) including high density Poly Ethylene (HDPE), Cyclic Olefin Copolymer (COC), Poly Vinyl Chloride (PVC), Poly Vinylidene Chloride (PVDC), or flour polymers.

The length of the package may be in the range of 110-240 mm, such as in the range of 140-230. Typically, the length of a package for a female catheter may be in the low end of the range, whereas the length of a package for a male catheter may be in the upper end of the range. The diameter of the package may be in the range of 15-35 mm.

The length of the container may typically be sufficient to ensure that a person using the catheter assembly can grip around the container with at least three fingers while removing the cover from the container. Thus, the length of the cover may as an example constitutes at least 70% of the length of the container to facilitate gripping of both parts when removing the cover from the container when opening the assembly.

In order to achieve a compact assembly, at least a part of the cavity may extend over at least a part of the accommodation. This may further facilitate arrangement of at least a part of the collecting bag around the catheter, whereby the bag may effectively shield at least a part hereof.

As the bag in the folded configuration may be thicker and may have a more compact form due to the folding and coiling of the bag around least a part of the accommodation compared to an unfolded bag, the folded and coiled bag may be easier to grip, hold, and handle, and may thus act as a handle for the catheter. In one embodiment, the dimension of the collecting bag in a direction being transverse to a longitudinal direction of the package is at least 25% of the diameter of the cover. In embodiments, holding means may be provided on an exterior surface of the collecting bag to avoid or be able to control the unfolding of the bag for the use situation. Such holding means may be, but are not limited to, tape, tape connections, hook-and-loop, microbuttons, buttons or other suitable types.

The container may comprise a neck portion with an outer diameter of maximum 60% of the outer diameter of the container. Due to the smaller diameter of the neck portion, the collecting bag may be folded and coiled about the neck portion without essentially increasing the total diameter of the package.

As the catheter may be a hydrophilic catheter, the accommodation may contain an amount of a liquid swelling medium being sufficient for rendering a surface of the catheter low-frictional. Thereby, it is possible to reduce or avoid the risks of health and discomfort like inflammatory damage and degeneration caused by the medical device.

By a hydrophilic urinary catheter is herein meant a catheter of the kind having on at least a part of its surface a surface layer intended to produce a low-friction surface character of the catheter by treatment with a liquid swelling medium prior to the use hereof.

I.e. a ready-to-use assembly may be facilitated by providing in the package a liquid medium, e.g. a swelling medium for rendering the coating of the catheter slippery, or an antiseptic solution, a pain relieving solution or any kind of pharmaceutical or non-pharmaceutical medicament. This medium should, however, be present around the insertable part of the catheter for collecting urine and should therefore be prevented from flowing into the collecting bag. Thus, the package or the catheter itself may comprise flow preventing means to prevent flow of the medium to the collecting bag. As an example, these flow preventing means may comprise a sealing structure which forms part of the package and which is thereby automatically removed from the catheter upon exposure of the insertable part of the catheter from the package, or upon complete removal of the catheter from the package.

The container may form an opening into the accommodation through which opening the catheter may be positioned in the accommodation and through which the catheter may be removed from the accommodation. The catheter and the container may be formed so that the catheter forms a closure for the opening. Thereby, it may be achieved that the catheter assembly is easily assembled and it may be prevented that the accommodation is contaminated. To ensure closing of the opening, the catheter may comprise a solid part of a size which fits the size of the opening. The opening may be formed in the neck portion of the container, thereby allowing for a smaller opening into the accommodation.

By forming the catheter and the container so that the catheter forms a closure for the opening, it may further be achieved that the catheter is positioned in the container so that no or at least only a very small axial displacement of the catheter is possible. This may further protect the catheter and ensure that the coating is not damaged due to contact between the catheter and the inner walls of the container.

As it is crucial that the insertable part of the catheter is not contaminated, e.g. by a user unintentionally touching it or if the insertable part touches surrounding obstacles, it may be an advantage if the catheter is fixed to the opening by a screw-threaded catheter-joint. Thereby, it may be achieved that the catheter remains in the container when removing the cover from the container, so that it is not unintentionally removed together with the cover. Furthermore, it may be achieved that the collecting bag can be unfolded and prepared for use before the catheter is removed from the accommodation.

However, as an alternative, the cover may be used as a handle, when removing the catheter from the accommodation. This may be achieved by providing friction between the collecting bag and the inner surface of the cover of a size which ensures that the bag sticks to the cover when removing the cover from the container. Thus, the catheter may be manipulated by use of the cover.

A screw-threaded catheter-joint may also facilitate positioning and removal of the catheter in and from the accommodation, as this joint may help a user having reduced dexterity and in particular a user which is prevented from using both hands.

A screw-threaded catheter-joint may further provide a more compact assembly, as the size of the catheter-joint may be smaller when provided as a screw-threaded joint compared to other types of joints which may require a larger size of the catheter package to ensure a sufficient closing hereof.

The closure formed by the catheter may be liquid tight to prevent a liquid medium, such as a swelling medium to leak from the accommodation.

To facilitate removal of the cover from the container, the cover may be releasably fixed to the container also by a screw-threaded cover-joint, further facilitating single-handed use of the assembly. This may further also facilitate closing of the package after use, when returning the catheter into the accommodation. Before closing the cover, the catheter and the collecting bag may be separated. This may be achieved by arranging a rupture line at a position of the bag, at which section the two parts may be easily separated. Alternatively, the collecting bag may be emptied and the bag may subsequently be returned to the package together with the catheter.

When fixing the cover to the container after use of the catheter, it may be an advantage if a liquid medium in the container remains herein and does not leak. This may be achieved by providing a cover-joint that is liquid tight. Furthermore, a liquid tight cover-joint may prevent contamination of the inner part of the package and thus the catheter and the collecting bag before use hereof.

It is an advantage to provide the catheter package in a material that is at least substantially gas impermeable and which is durable to at least moderate variations in external conditions such as temperature variations and light to protect the catheter and to avoid contamination hereof. It should be understood that by gas impermeable is meant gas impermeable under normal conditions for use of a catheter. I.e. by providing a gas impermeable catheter package evaporation of a liquid medium present in the accommodation may be prevented, e.g. for a storage time of 1, 2, 3, or more years or whatever is desired for the catheter. However, in one embodiment, only the container is provided as substantially gas impermeable, as no liquid is present in the cover. As a consequence, the cover may be provided with a lower thickness of the material than the container. The material thickness of the container and the cover may typically be in the range of 0.3-2.0 mm.

To protect the insertable part of the catheter, the container may have an elongated shape such that the insertable part of the catheter can be accommodated in a substantially linear orientation. Thus, it may be ensured that the insertable part is not bent, curled, buckled, or otherwise damaged. In case the catheter is a telescopic catheter, the catheter may be accommodated in a substantially linear orientation in the non-extended configuration to obtain a compact assembly.

The collecting bag may be connected to the catheter in various ways. In one embodiment, the bag is attached to the closure. As the closure may comprise a solid part enabling closing of the opening into the accommodation, it may be an advantage to connect the bag to this solid part, as this may facilitate sound connection between the catheter and the collecting bag.

As some users of the assembly may have reduced dexterity, it may be an advantage if the collecting bag forms a textured outer surface around the closure, as the textured surface may enhance gripping possibilities for the user.

Furthermore, the outer surface of the container and the cover may be provided with a texture to enhance gripping possibilities and if necessary facilitate opening of the package by one hand only.

The container and cover may form a hardbox around the catheter and collecting bag. This may especially be an advantage for disabled users, such as paraplegics or tetraplegics, who typically have to bring along one or more assemblies when leaving home. A hardbox may protect the catheter and the bag, in a way that they are not damaged or contaminated. Thus, a hardbox may facilitate a ready-to-use assembly. Moreover, a hard-box may also allow for alternative embodiments wherein the cover can be broken apart from the container, also facilitating single-handed use. Such embodiments may be particularly well suited for single-handed use if at least part of the exterior surface, of at least one of the cover and the container, is formed or shaped so as to provide a suitable surface for applying the necessary force to break the parts apart by means of the fingers of one hand only. This may include, but is not limited to, providing a geometrical shape, e.g. a triangular or rectangular shape, and/or a decreased or increased dimension of at least part of the exterior surface of the cover or the container, thereby facilitating a suitable "breaking surface". The parts may, as an example, be made breakable by means of incorporation of a band of thinner material thickness between the cover and the container (in or on the transition between the parts).

The hardbox may further provide the advantage that evaporation of liquid, such as a swelling medium, from the accommodation may be reduced, whereby the storage time for e.g. a hydrophilic catheter in the catheter package may be prolonged. Furthermore, tamper-evidence means, such as, but not limited to, a band or strip of tape at least partly covering the transition between the container and the cover may be provided. This allows the user to detect any premature separation of the cover and the container thereby avoiding use of a contaminated assembly.

The catheter may be a telescopic catheter, i.e. a catheter made in two separate parts being joined in a telescopic joint. As a telescopic catheter has to be extended before use, the container may comprise releasing means for extending the catheter during removal from the accommodation. Thereby, the catheter is ready to be inserted upon removal from the accommodation, without the user having to touch the insertable part of the catheter or otherwise manually ensure extension hereof.

The releasing means may e.g. be means for fixing one of the parts to the inner part of the accommodation. When removing the catheter from the accommodation by pulling the free end, the catheter will extend until fully extended and locking of the two separate parts has been completed. Then, as the pulling force continues, the force acting on the fixing means increases until the breaking strength hereof is reached, and thus the fixing means breaks. As a consequence, the catheter can be removed from the accommodation in an extended configuration. The releasing means may be very similar to those disclosed European Application No. 1 893 275.

By locking of the two separate parts should be understood that the two parts are interlocked so that they do no longer slide relative to each other. To ensure safe use of the telescopic catheter, it is desirable that the interlocking of the two separate parts should be sufficient to provide a catheter, which does not collapse during insertion into the urethra, i.e. the force which is required to collapse the catheter should be higher than the force required to insert the catheter into the urethra. The coupling between the two parts should be sufficiently strong to maintain the expanded configuration during bending of the catheter as it is entered through the curved passage of the urethra. The coupling means may be very similar to those disclosed in International Application published as WO 2008/138351 or International Application published as WO 2008/138352.

A telescopic catheter may provide a more compact assembly and thereby improve convenience for the users of the assembly both at home and on the road.

The container may facilitate relocation of an extended catheter in the accommodation. This may e.g. be achieved by deforming the catheter against the walls of the hardbox, as the insertable part of the catheter may bend upon insertion hereof back into the accommodation of the container. The container may thus be of a size which allows bending of the insertable part. To facilitate bending of the insertable part, the bottom part of the container may have an inner surface with rounded corners, in a way that the insertable part may easily bend upwards when reaching the bottom of the container. As an alternative the bottom part of the container may have an inner surface without rounded surfaces, in a way that the tip end of the insertable part of the catheter may be at least partly retained at the bottom when reaching the bottom of the container. By continued pushing of the catheter back into the accommodation, the interlocking between the two parts of the telescopic catheter may break so that the expanded configuration of the catheter is no longer maintained.

Also for none-telescopic catheters, the hardbox may facilitate relocation of the catheter, as the walls of the hardbox may act as guidance for the catheter and thereby facilitate re-sealing hereof.

The cover and container may be provided with different appearance so that a user can easily distinguish between the two parts of the package. As an example, the bottom of the container may be flat which further facilitates that the package can be positioned in an upright position, whereas the upper part of the cover may be convex which also facilitates correct positioning of the package when removing the cover from the container. If the package is turned upside down, the liquid in the container may be spilled.

BRIEF DESCRIPTION OF THE DRAWINGS

Embodiments of the invention will now be further described with reference to the drawings, in which.

DETAILED DESCRIPTION OF THE DRAWINGS

It should be understood that the detailed description and specific examples, while indicating embodiments of the invention, are given by way of illustration only, since various changes and modifications within the spirit and scope of the invention will become apparent to those skilled in the art from this detailed description.

Figure 1A:
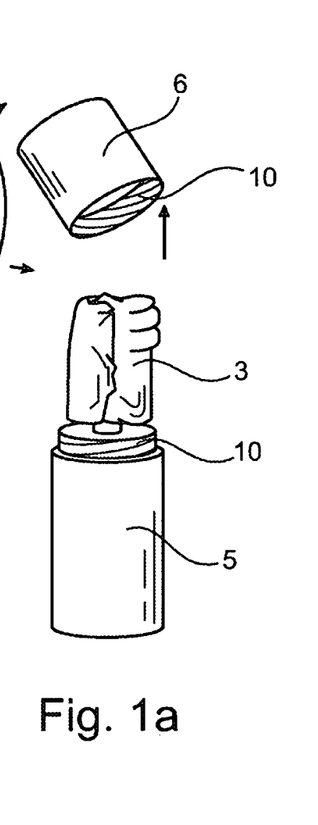
FIGS. 1a and 1b illustrate a urinary catheter assembly.
Figure 1B:
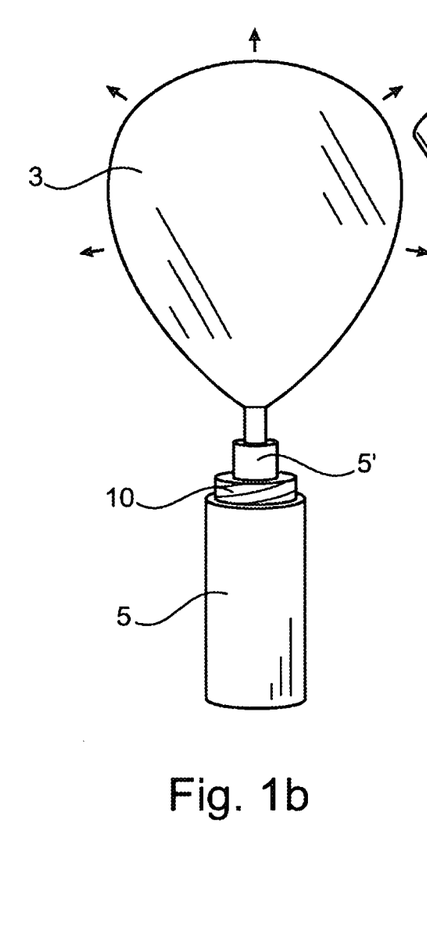

FIGS. 1a and 1b illustrate a urinary catheter assembly 1, which comprises a urinary catheter 2 (see FIG. 2) and a collecting bag 3. The urinary catheter 2 is for collecting urine from a body opening and the collecting bag 3 is thus connected to the catheter, in a way that a urinary flow can be established in a flow path from the catheter into the collecting bag.

The assembly 1 further comprises a catheter package comprising a container 5 and a cover 6. The container 5 forms an accommodation 7 (see FIG. 3) for an insertable part 8 of the catheter, whereas the cover 6, which may be seen as a lid, forms a cavity 9 for the collecting bag 3.

The collecting bag 3 comprises a compartment between sheets of a foil material. The collecting bag 3 is in a folded and coiled configuration in the cavity 9 before the cover 6 is detached from the container 5 (see FIG. 1a). In order to keep the collecting bag folded and coiled, holding means such as a Velcro® connection may be provided on the exterior surface of the bag (not shown). The connection may of course be placed so as to take into account the way the collecting bag is folded. FIG. 1b illustrates the collecting bag 3 in an unfolded configuration, while the insertable part 8 of the catheter 2 is still in the container 5.

The cover 6 is releasably fixed to the container 5 by a screw-threaded cover-joint 10.

The container 5 forms an opening into the accommodation 7 through which opening the catheter 2 can be positioned in the accommodation 7 and through which the catheter 2 may be removed from the accommodation 7. In the illustrated embodiment, the opening is formed in a neck portion 5' of the container 5. The catheter 2 and the container 5 are formed, in a way that the catheter 2 forms a closure for the opening.

As it is crucial that the insertable part 8 of the catheter 2 is not contaminated, e.g. by a user unintentionally touching it or if the insertable part touches surrounding obstacles, the catheter 2 is advantageously fixed to the opening by a screw-threaded catheter-joint (not shown). Thereby, it can easily be achieved that the catheter 2 remains in the container 5 when removing the cover 6 from the container 5, so that it is not unintentionally removed together with the cover. Furthermore, it may be achieved that the collecting bag 3 can be unfolded and prepared for use before the catheter 2 is removed from the accommodation 7.

The container 5 and cover 6 form a hardbox around the catheter 2 and collecting bag 3. A hardbox protects the catheter 2 and the bag 3 so that they are not damaged or contaminated. Thus, a hardbox may facilitate a ready-to-use assembly 1. Tamper-evidence means, e.g. a strip of tape, may be provided on the transition between the container and the cover, so that it is evident to a user if the assembly has already been opened (not shown).

The hardbox further provides the advantage that evaporation of liquid 11 (see FIG. 3), such as a swelling medium, from the accommodation 7 can be reduced, whereby the storage time for e.g. a hydrophilic catheter in the catheter package 5, 6 can be prolonged.

Figure 2:
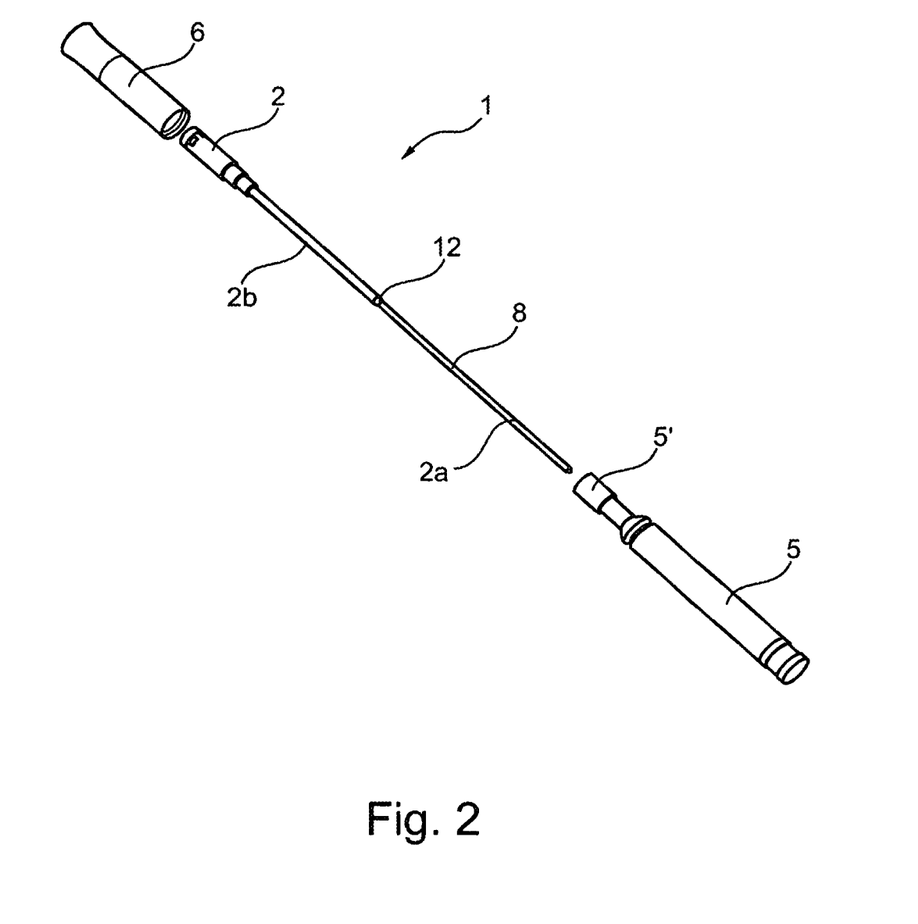
FIG. 2 illustrates the urinary catheter assembly without the collecting bag.

FIG. 2 illustrates an embodiment of a urinary catheter assembly 1 without the collecting bag. In the illustrated embodiment, the catheter is a telescopic catheter made in two separate parts 2a, 2b being joined in a telescopic joint 12. As a telescopic catheter has to be extended before use, the container 5 comprises releasing means (not shown) for extending the catheter during removal from the accommodation. Thereby, the catheter 2 is ready to be inserted upon removal from the accommodation 7 without the user has to touch the insertable part 8 of the catheter 2 or otherwise manually ensure extension hereof.

Figure 3:
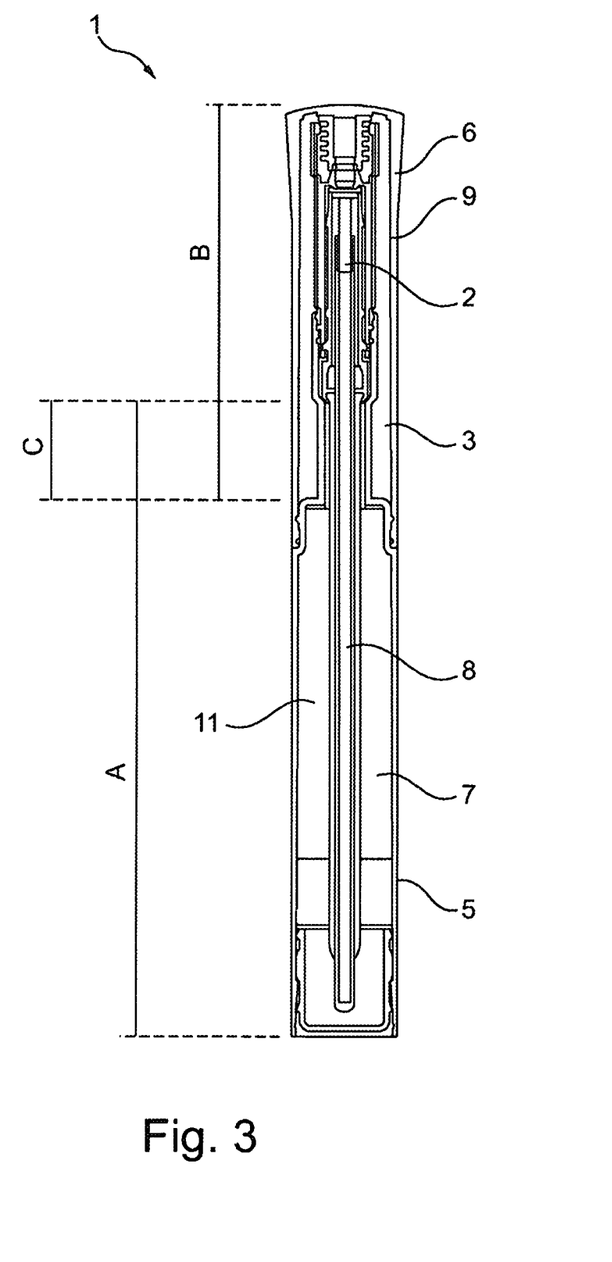
FIG. 3 illustrates a cross-section along the longitudinal direction of the assembly.

FIG. 3 illustrates a cross-section along the longitudinal direction of the assembly 1 before removal of the cover 6 from the container 5. The collecting bag 3 is positioned in the cavity 9 of the cover 6 in a folded configuration, whereas the insertable part 8 of the catheter is positioned in the accommodation 7 formed by the container 5.

To provide a compact assembly 1, the package forms an overlap C in which the cavity 9 partly covers the accommodation 7. This is illustrated by the letters A, B, and C, where A indicates the length of the accommodation 7, B indicates the length of the cavity 8, and C indicates the overlap there between. The compact assembly 1 is achieved by folding a part of the collecting bag 3 around a part of the catheter 2 when arranging the catheter 2 and the collecting bag 3 in the package 5, 6. Due to the overlap C, the total length of the package 5, 6 is reduced.

Figure 4:
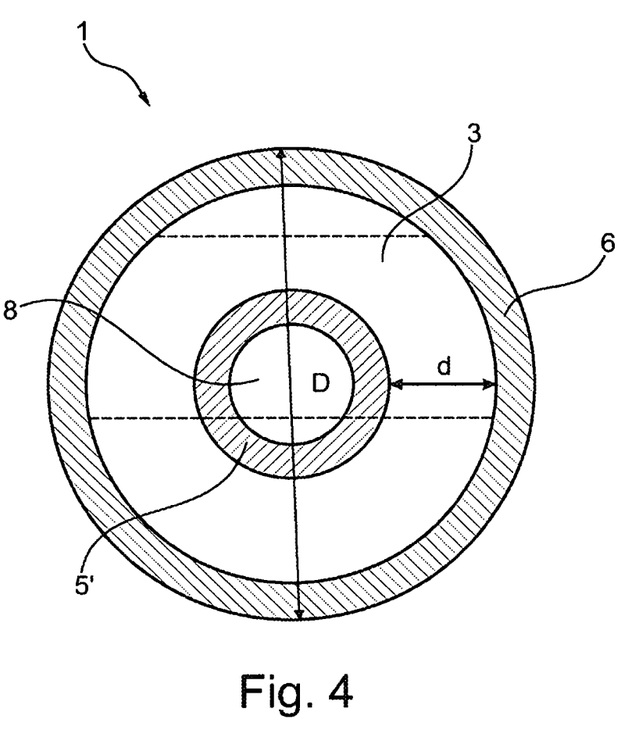
FIG. 4 illustrates a cross-section across the assembly.

FIG. 4 illustrates a cross-section across the assembly 1 from which it can be seen that the collecting bag 3 is folded and coiled around a part of the insertable part 8 of the catheter 2 and the neck portion 5' of the container 5. In the illustrated embodiment, the dimension d of the collecting bag 3 in a direction being transverse to a longitudinal direction of the package is at least 25% of the diameter D of the cover 3. It should be understood that the longitudinal, direction of the package 5, 6 is the direction substantially parallel to the longest dimension of the package. It should further be underlined that FIG. 4 is not to scale as it is for illustration only.

Figure 5A:
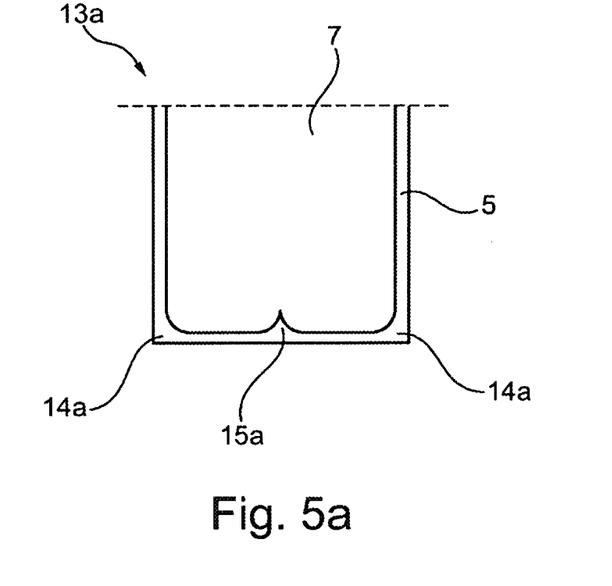
FIGS. 5a and 5b illustrate a section of two different embodiments of a container.
Figure 5B:
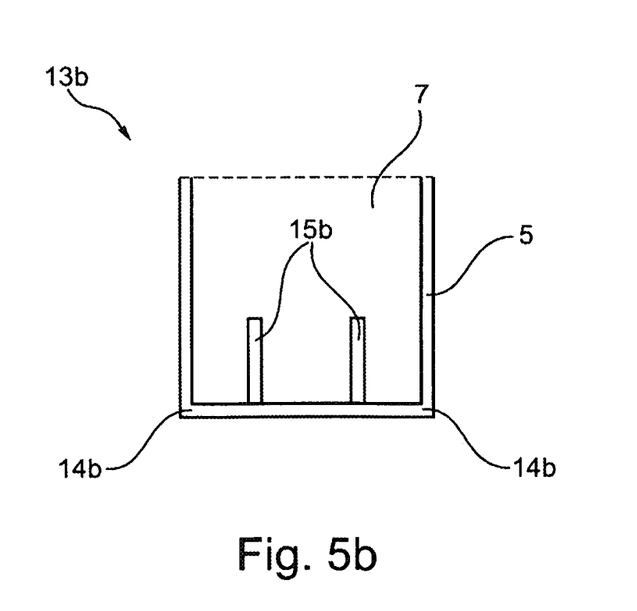

FIGS. 5a and 5b illustrate a bottom section 13a, 13b of two different embodiments of a container 5. The bottom sections 13a, 13b facilitate relocation of an extended catheter in the accommodation in two different ways. In FIG. 5a it is done by deforming the insertable part 8 of the catheter 2 against the walls of the container 5, as the insertable part 8 of the catheter is bent upon insertion hereof back into the accommodation of the container. To facilitate bending of the insertable part 2, the bottom part 13*a* of the container has an inner surface with rounded corners 14*a* so that the insertable part 8 easily bends upwards when reaching the bottom of the container 5.

An alternative bottom section 13*b* is illustrated in FIG. 5*b*, where the bottom part of the container 5 has an inner surface without rounded corners 14*b* so that the tip end of the insertable part 2 of the catheter may be al least partly retained at the corner 14*b* when reaching the bottom of the container. By continued pushing of the catheter 2 back into the accommodation 7, the interlocking between the two parts of the telescopic catheter may break so that the expanded configuration of the catheter 2 is no longer maintained.

In the illustrated embodiments of FIGS. 5*a* and 5*b*, the bottom sections comprise protrusion(s) 15*a*, 15*b* at the bottom part. These protrusions 15*a*, 15*b* will further facilitate relocation of an extended catheter 2 in the accommodation, as the protrusions 15*a*, 15*b* will enhance the function of the corners 14*a*, 14*b* as the effective area of the bottom is decreased.

In a second aspect of the invention, it is an object of the embodiments of the second aspect to provide an improved urinary catheter assembly, and particularly, to provide a more easy-to-handle assembly.

In the second aspect, the invention provides a urinary catheter assembly comprising at least one urinary catheter for collecting urine from a body opening and a collecting bag connected to the catheter in a way that a urinary flow can be established in a flow path from the catheter into the bag, the container forming an accommodation for an insertable part of the catheter, the cover forming a cavity for the collecting bag, and the cover being releasably fixed to the container, wherein the container forms an opening into the accommodation and wherein the catheter forms a closure which is joined to the opening.

To provide a more easy-to-handle assembly, the container forms an opening into the accommodation and the catheter forms a closure which is joined to the opening as this may facilitate removal of the catheter by the use of only one hand. This may further prevent the accommodation from being contaminated. To ensure closing of the opening, the catheter may comprise a solid part of a size which fits the size of the opening. The opening may be formed in a neck portion of the container, thereby allowing for a smaller opening into the accommodation.

Embodiments of the Second Aspect

EMB. 1. A urinary catheter assembly comprising at least one urinary catheter for collecting urine from a body opening and a collecting bag connected to the catheter, in a way that a urinary flow can be established in a flow path from the catheter into the bag, the assembly further comprising a catheter package with a container and a cover, the container forming an accommodation for an insertable part of the catheter, the cover forming a cavity for the collecting bag, and the cover being releasably fixed to the container, wherein the container forms an opening into the accommodation and wherein the catheter forms a closure which is joined to the opening.

EMB. 2. An assembly according to the first embodiment, wherein the catheter is fixed to the opening by a screw-threaded catheter-joint.

EMB. 3. An assembly according to any of the preceding embodiments, wherein the joint between the catheter and the opening provides a solid fixation of the catheter in the opening, in a way that the cover can be removed from the container without removing the catheter from the opening.

EMB. 4. An assembly according to any of the preceding embodiments, wherein the package forms an overlap in which the cavity extends about the accommodation.

EMB. 5. An assembly according to any of the preceding embodiments, wherein the catheter is a hydrophilic catheter and wherein the accommodation comprises an amount of a liquid swelling medium being sufficient for rendering a surface of the catheter low-frictional.

EMB. 6. An assembly according to any of the preceding embodiments, wherein the joint between the closure and the opening is liquid tight.

EMB. 7. An assembly according to any of the preceding embodiments, wherein the bag is attached to the closure.

EMB. 8. An assembly according to embodiment 7, wherein the bag forms a textured outer surface around the closure.

EMB. 9. An assembly according to any of the preceding embodiments, wherein the container and cover form a hardbox around the catheter and bag.

EMB. 10. An assembly according to any of the preceding embodiments, wherein the catheter is telescopic and wherein the container comprises releasing means for extending the catheter during removal from the accommodation.

EMB. 11. An assembly according to embodiment 10, wherein the container facilitates relocation of an extended catheter in the accommodation.

In a third aspect of the invention it is an object of embodiments of the third aspect to provide an improved urinary catheter assembly and, particularly, to provide a flexible and ready-to-use assembly.

In the third aspect, the invention provides a urinary catheter assembly comprising at least one urinary catheter for collecting urine from a body opening and a collecting bag connected to the catheter in a way that a urinary flow can be established in a flow path from the catheter into the bag, the assembly further comprising a catheter package with a container and a cover, the container forming an accommodation for an insertable part of the catheter, the cover forming a cavity for the collecting bag, and the cover being releasably fixed to the container, wherein the catheter is a hydrophilic compact catheter and the accommodation comprises an amount of a liquid swelling medium being sufficient for rendering a surface of the catheter low-frictional.

A ready-to-use assembly may be further facilitated by providing in the catheter package an antiseptic solution, a pain relieving solution or any kind of pharmaceutical or non-pharmaceutical medicament in addition to the liquid swelling medium. This medium should, however, be present around the insertable part of the catheter for collecting urine and should, therefore, be prevented from flowing into the collecting bag. Thus, the package or the catheter itself may comprise flow preventing means in order to prevent flow of the medium to the collecting bag. As an example, these flow preventing means may comprise a sealing structure, which forms part of the package and which is thereby automatically removed from the catheter upon exposure of the insertable part of the catheter from the package, or upon complete removal of the catheter from the package.

Embodiments of the Third Aspect

EMB. 20. A urinary catheter assembly comprising at least one urinary catheter for collecting urine from a body opening and a collecting bag connected to the catheter in a way that a urinary flow can be established in a flow path from the catheter into the bag, the assembly further comprising a catheter package with a container and a cover, the container forming an accommodation for an insertable part of the catheter, the cover forming a cavity for the collecting bag, and the cover being releasably fixed to the container, wherein the catheter is a hydrophilic compact catheter and the accommodation comprises an amount of a liquid swelling medium being sufficient for rendering a surface of the catheter low-frictional.

EMB. 21. An assembly according to embodiment 1, wherein the container and cover form a hardbox around the compact catheter and bag.

EMB. 22. An assembly according to any of embodiments 20 or 21, wherein the compact catheter is made in two separate parts joined in a telescopic joint.

EMB. 23. An assembly according to embodiment 22, wherein the container comprises releasing means for extending the catheter during removal from the accommodation.

EMB. 24. An assembly according to any of the preceding embodiments, wherein the container facilitates relocation of the compact catheter in the accommodation.

EMB. 25. An assembly according to any of the preceding embodiments, wherein the package forms an overlap in which the cavity partly covers the accommodation.

EMB. 26. An assembly according to any of the preceding embodiments, wherein the container forms an opening into the accommodation and wherein the catheter forms a closure to said opening when the assembly is stored which closure is joined to the opening.

EMB. 27. An assembly according to any of the preceding embodiments, wherein the catheter is fixed to the opening by a screw-threaded catheter-joint.

EMB. 28. An assembly according to any of the preceding embodiments, wherein the joint between the catheter and the opening provides a solid fixation of the catheter in the opening in a way that the cover can be removed from the container without removing the catheter from the opening.

EMB. 29. An assembly according to any of the preceding embodiments, wherein the joint between the closure and the opening is liquid tight.

EMB. 30. An assembly according to any of the preceding embodiments, wherein the bag is attached to the closure.

EMB. 31. An assembly according to embodiment 30, wherein the bag forms a textured outer surface around the closure.

The invention claimed is:

1. A urinary catheter assembly comprising:
   a catheter having a proximal portion insertable into a body and adapted for collecting urine from a body opening and a urine collecting bag connected to the catheter;
   a catheter package including a container and a cover attachable to the container, the container includes a bottom located at a distal end and a neck portion located at a proximal end and a cover joint located between the distal end and the proximal end of the container, where the neck portion forms an opening into an accommodation that is sized to receive the proximal portion of the catheter, and the cover forms a cavity for the urine collecting bag and is releasably fixed to the cover joint of the container;
   wherein the package forms an overlap in which the cavity of the cover partly covers the accommodation;
   wherein the catheter and the neck portion combine to provide a seal that prevents liquid from flowing out from the accommodation through the opening in the neck portion.

2. An assembly according to claim 1, wherein the overlap is at least 10% of a total length of the catheter package.

3. An assembly according to claim 1, wherein at least a part of the cavity extends over at least a part of the accommodation.

4. An assembly according to claim 1, wherein the urine collecting bag is retained in the package inside of the cavity of the cover and between the neck portion of the container and the cover.

5. An assembly according to claim 1, wherein the neck portion of the container has an outer diameter that is a maximum 60% of the constant outer diameter of the container.

6. An assembly according to claim 1, wherein the catheter is a hydrophilic catheter and wherein the accommodation contains an amount of a liquid adapted to wet the hydrophilic catheter.

7. An assembly according to claim 1, wherein the catheter and the neck portion combine to provide a threaded catheter-joint seal.

8. An assembly according to claim 1, wherein the seal forms a liquid tight closure for the opening into the accommodation.

9. An assembly according to claim 1, wherein the cover is releasably fixed to the cover joint of the container by a threaded cover-joint.

10. An assembly according to claim 9, wherein the threaded cover-joint is liquid tight.

11. An assembly according to claim 1, wherein the catheter package is gas impermeable.

12. An assembly according to claim 1, wherein the proximal portion of the catheter is retained in the accommodation in a substantially linear orientation.

13. An assembly according to claim 1, wherein the container and the cover form a hardbox around the catheter and the urine collecting bag.

14. An assembly according to claim 1, wherein the catheter is telescopic and wherein the container comprises releasing means for extending the catheter during removal from the accommodation.

15. An assembly according to claim 14, wherein the container facilitates relocation of an extended catheter in the accommodation.

16. An assembly according to claim 1, wherein the container has a constant outer diameter between the bottom located at the distal end and the cover joint.

* * * * *